United States Patent [19]

Grönberg et al.

[11] Patent Number: 4,573,181

[45] Date of Patent: Feb. 25, 1986

[54] X-RAY FLUORESCENCE ANALYZERS

[75] Inventors: Thomas Grönberg, Södra Sandby; Torsten Almen, Malmö, both of Sweden; Klaes Golman, Rungsted, Denmark; Sören Mattsson, Lund; Staffan Sjöberg, Malmö, both of Sweden

[73] Assignee: Elementanalys Almen & Gronberg AB, Sweden

[21] Appl. No.: 455,842

[22] Filed: Jan. 5, 1983

[30] Foreign Application Priority Data

Jan. 12, 1982 [SE] Sweden ............................. 8200121

[51] Int. Cl.$^4$ ........................................... G01N 23/22
[52] U.S. Cl. .......................................... 378/45; 378/53
[58] Field of Search ........................... 378/45, 44–48, 378/53, 83, 88, 99, 6, 46; 364/414, 577; 250/169; 358/111

[56] References Cited

U.S. PATENT DOCUMENTS

| 3,389,254 | 6/1968 | Russell | 250/369 |
| 3,493,750 | 2/1970 | Morgan | 250/369 |
| 3,688,110 | 8/1972 | Severance | 378/46 |

FOREIGN PATENT DOCUMENTS 0129735  3/1979  Japan ..................... 378/45

OTHER PUBLICATIONS

*Radiology*, vol. 99, Apr. 1971, p. 117, Abstract, Hoffer, Paul B., Gottschalk, Alexander, "Fluorescent Thyroid Scanning: Scanning Without Radioisotopes,".

Primary Examiner—Craig E. Church
Assistant Examiner—Charles F. Wieland
Attorney, Agent, or Firm—Shapiro and Shapiro

[57] ABSTRACT

An apparatus for determining the content of an element having an atomic number higher than 47, in a sample volume, in particular for determining the concentration of an X-ray contrast agent in vivo, employs a radiation source for such excitation of the element in the sample volume with collimated radiation that the element emits its characteristic X-ray radiation. An NaI(T1) scintillation detector is directed towards the sample volume for receiving X-ray radiation therefrom at an angle of from 90° to 135° in relation to the excitation radiation. Both the energy of Copton-scattered photons in the sample and the difference between this energy and 28.5 KeV must be clearly distinguished from the characteristic energy of the element concerned. A first single-channel analyzer registers the number of pulses of the detector within a predetermined energy interval about the energy value for the characteristic X-ray radiation of the element concerned, and two further single-channel analyzers register the number of pulses at the limits of the interval mentioned. A calculating unit in the form of computer determines the background radiation in the interval mentioned using the two latter pulse numbers, and determines the content of the element concerned from the difference between the pulse number of the first analyzer and the pulse number representing the background radiation.

2 Claims, 5 Drawing Figures

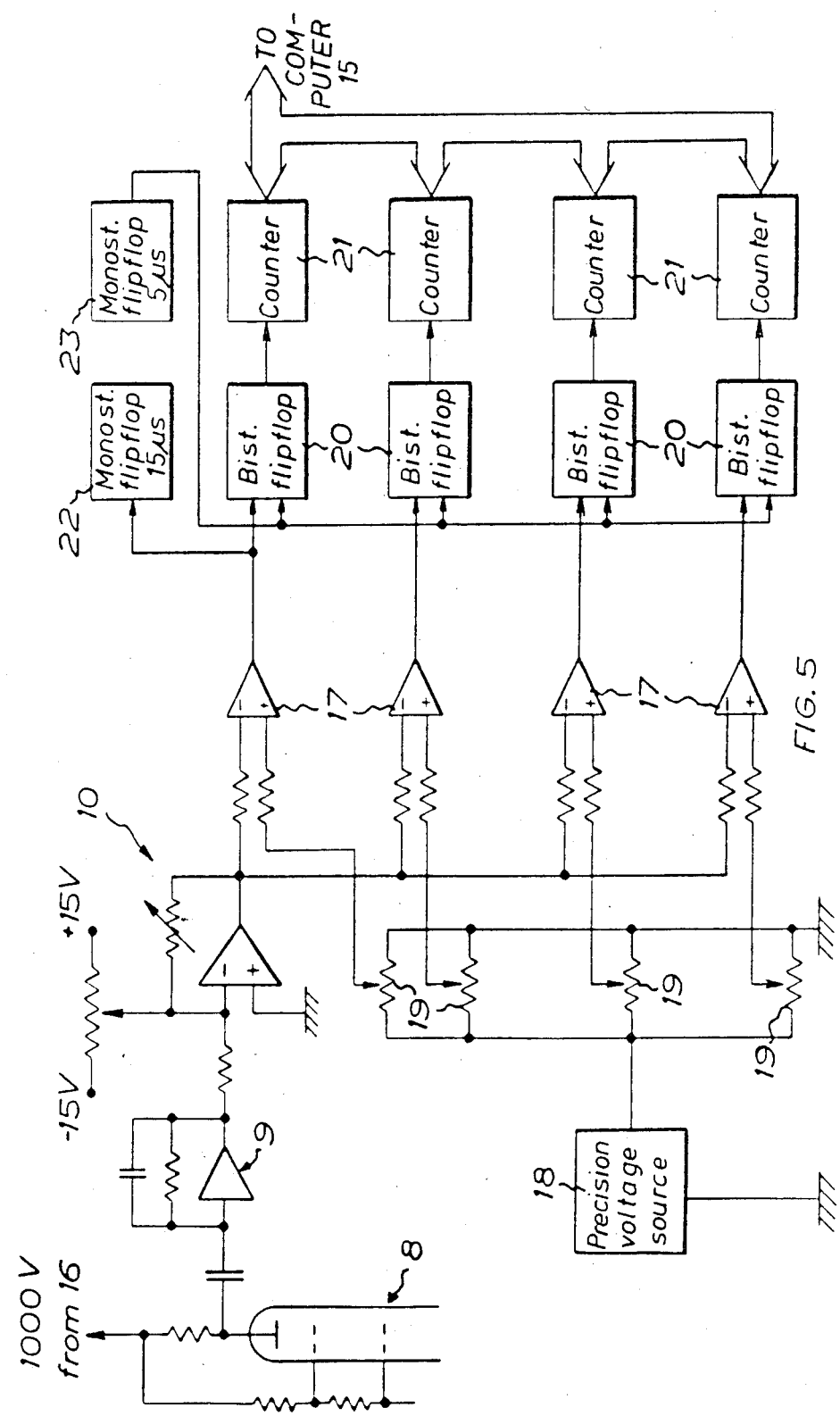

X-RAY FLUORESCENCE ANALYZERS

BACKGROUND OF THE INVENTION

The present invention generally relates to an apparatus for determining the content of a stable element in a sample volume using X-ray fluorescence. The elements concerned are those having atomic numbers (atomic numbers in the periodic system) higher than 47. The invention particularly relates to the determination in vivo of the concentration of iodic X-ray contrast agents.

By comparative tests, it has been established that X-ray fluorescence technology used for quantitative measurements in vivo of the concentration of iodic X-ray contrast agents in well blood-filled soft tissue, may provide a measurement of the body's rate of excreting the contrast agent. This excretion rate reflects in its turn the function of the kidneys. Thus, the renal function may be determined by repeated measurements of the concentration of the contrast agent in the soft tissue.

In such X-ray fluorescence analysis, use has been made of int.al. $^{241}$Am as excitation radiation source, and a Ge(Li) detector has been employed for registering the characteristic $K_\alpha$ X-ray radiation from iodine. This employed detector, however, is difficult to operate, bulky and expensive and moreover requires low prevalent temperatures. Therefore, it is not suited for use in a mass-produced apparatus for carrying out large-scale measurements. It would be desirable to be able to employ, for example, an NaI(Tl) detector instead of the Ge(Li) detector. However, the NaI(Tl) detector suffers from the drawback that registration of the $K_\alpha$ X-ray radiation characteristic of iodine, which is emitted from the contrast agent will be overlaid by the registration of Compton-scattered photons in the sample, which interact with iodine atoms in the detector crystal proper.

SUMMARY OF THE INVENTION

One object of the present invention is to provide an apparatus of the type disclosed by way of introduction, the apparatus overcoming the above-described drawbacks inherent in the Ge(Li) detector as well as the NaI(Tl) detector.

This and other objects of the present invention will be attained in that the above-described apparatus is given the characteristics which will appear from one or more of the appended claims.

BRIEF DESCRIPTION OF THE DRAWINGS

The invention will be described in greater detail below with reference to the accompanying drawings, in which:

FIG. 5 illustrates an embodiment of the electric circuits in the measuring apparatus of FIG. 4.

DESCRIPTION OF THE PREFERRED EMBODIMENT

Figure 1:
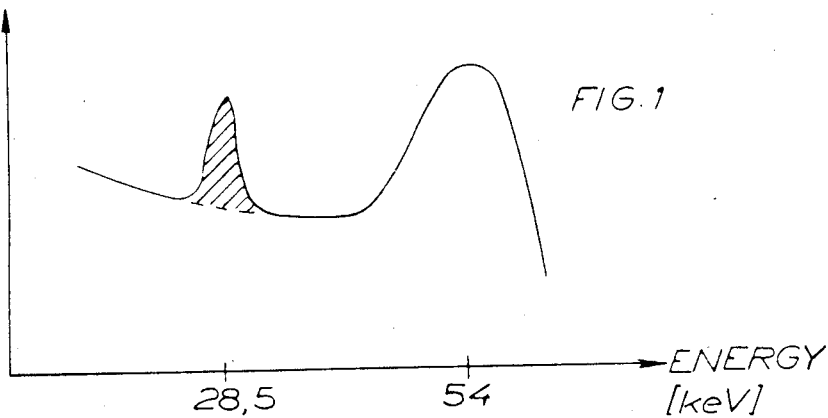
FIGS. 1-3 are pulse height distribution diagrams which serve to explain the function of the invention.

As was mentioned above, the renal function is decisive for the rate of excretion of, for example, X-ray contrast agents. In conjunction with, for example, kidney X-ray, angiography and computer tomography, this excretion rate can be determined using the temporal reduction in concentration of the contrast agent in soft tissue. In its turn, the concentration can be measured using X-ray fluorescence technology. For example, if $^{241}$Am is used as the source of radiation of an iodine-containing sample, the gamma radiation with a mean energy of 59.6 keV from this source will give rise to a $K_\alpha$ radiation characteristic of iodine with a mean energy of 28.5 keV from the sample. This characteristic X-ray radiation can be registered by means of a Ge(Li) detector, a pulse height or energy distribution according to FIG. 1 being obtained. In this instance, the detector is, in a conventional manner, directed so as to receive radiation at 90° in relation to the gamma radiation towards the sample. The hatched surface beneath the left-hand curve peak in FIG. 1 is proportional to the amount of iodine in the sample being examined. The surface beneath the right-hand curve peak in FIG. 1 is a measurement of 90° incoherently scattered photons from the sample and may be used for correcting the established iodine concentration with regard to geometric changes in the measuring arrangement.

Figure 2:
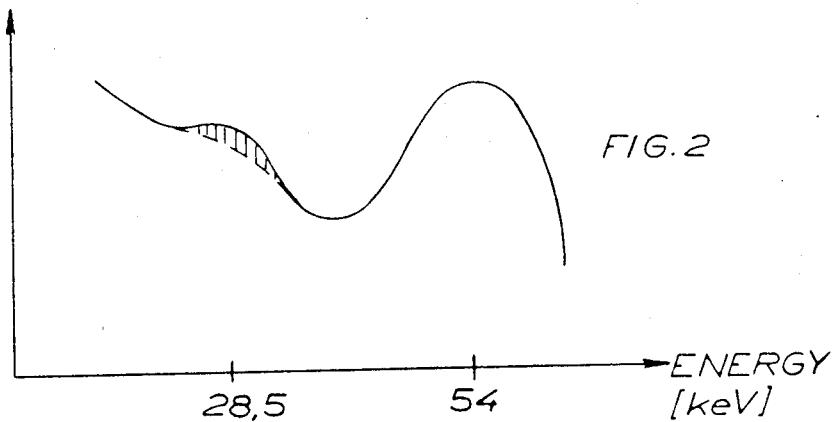

If the Ge(Li) detector in the above example is replaced by an NaI(Tl) detector, there will obtained a pulse height distribution according to FIG. 2. The right-hand peak on the curve in this figure once again represents Compton photons. The size of the left-hand peak in FIG. 2 is not, however, solely dependent upon the characteristic $K_\alpha$ radiation from the sample, but also upon disturbances consequential of so-called $I_{K\alpha}$ escape in the detector. In more precise terms, a portion of the Compton-scattered photons which reach the detector will be absorbed by interaction with the iodine atoms in the detector crystal, radiation characteristic of iodine (28.5 keV) being emitted in the crystal. If this characteristic radiation is in its turn absorbed completely in the crystal, there will be obtained, in the desired manner, a registration of the energy interval of about approximately 54 keV (this being the energy which the excited primary radiation from the $^{241}$Am preparation has after approximately 90° scattering). If, on the other hand, the characteristic radiation escapes from the crystal without interaction, there will be obtained a registration in the energy interval of about $54-28.5=25.5$ keV. This will entail such a powerful disturbance of the registration of the iodine-characteristic radiation with the mean energy of 28.5 keV that a determination of the iodine concentration in sample volume will not be possible.

The aim of the present invention is to distinguish, in terms of energy, the unavoidable disturbance from the energy interval of topical interest, i.e. the energy interval about 28.5 keV when iodine concentration is determined. This is attained according to the invention in that the angle between the primary radiation incident on the sample from the $^{241}$Am source and the radiation detected by the NaI(Tl) detector is made larger than 90° and is suitably placed in the interval of from 90° to 135°, in the case of iodine, preferably 135°. Using an angle of 135° there will be obtained a pulse height distribution according to FIG. 3. After scattering in the sample volume, the primary radiation from the $^{241}$Am preparation will in this case have an energy level of 50 keV, which entails that the unavoidable disturbance will occur at the interval about $50-28.5=21.5$ keV. Consequently, the disturbance has moved sufficiently far away from the energy interval of topical interest such that it will be possible to determine the iodine concentration in the sample volume.

By changing the angle between the primary radiation and the detected radiation, the pulse height distribution will also be changed in such a manner that the characteristic radiation of topical interest will fall on a part of the distribution curve which is relatively stable and, moreover, monotonous, in this case more precisely fading. This permits utilizing a fixed background correction upon calculation of the number of net pulses from the $K_{\alpha,\beta}$ radiation characteristic of iodine.

Thus, in accordance with the present invention, the angle between the primary radiation directed from the excitation source towards the sample volume and the radiation detected by the NaI(Tl) detector is rendered variable for an optimization of the detection geometry. In the case of determining the iodine concentration and employing a $^{241}$Am radiation source, the preferred angle is 135°. However, it is clear that, by selection of other sources of radiation and variations of the said angle, it is possible to detect other stable elements having atomic numbers from approximately 47 and higher. The criterion of selecting a radiation source and an angle between primary radiation and detective radiation is that both the energy of the Compton-scattered photons and the difference between the energy of the Compton-scattered photons and 28.5 KeV must be clearly distinguished from the energy of the characteristic X-ray radiation of the element concerned.

Figure 4:
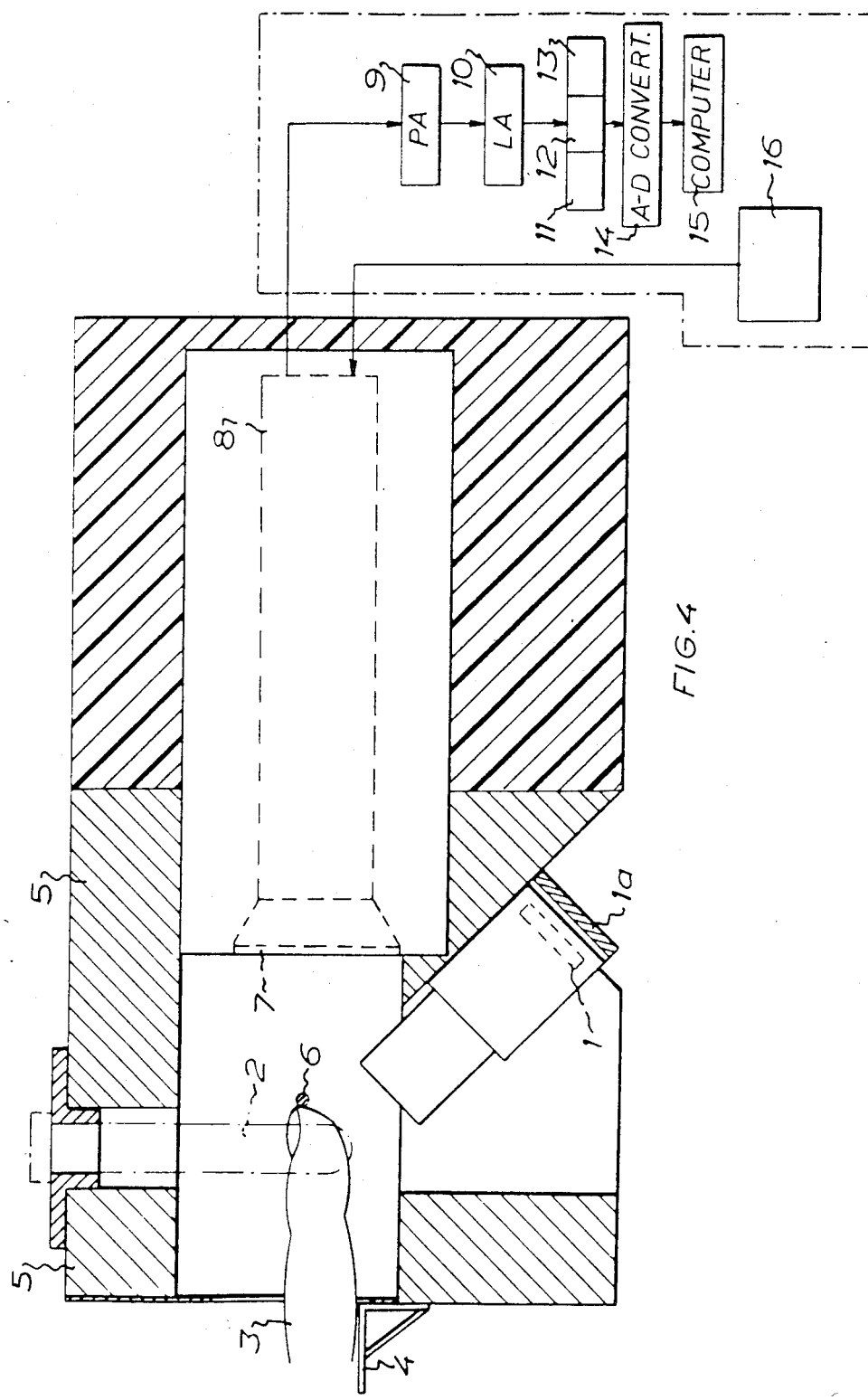
FIG. 4 is a block diagram of a measuring apparatus according to the invention.

One exemplifying embodiment of an apparatus according to the present invention is illustrated in FIG. 4. This apparatus is intended for determining the concentration of an iodine-containing contrast agent in the soft tissue portion at the tip of a finger. The iodine content of a test tube sample can also be determined. More precisely, the illustrated apparatus comprises a $^{241}$Am radiation source 1 which emits gamma radiation of an energy of approximately 60 keV. The radiation is collimated and directed towards a point where the bottom end of a test tube 2 can be placed or the tip of a finger 3 can be applied. For facilitating correct positioning of the finger tip, a finger support 4 is disposed at an insertion opening. In order to prevent undesirable radiation of the environment, a lead jacket 5 is arranged around the source of radiation and the sample area. A wire 6 is provided for the correct positioning of the finger. An NaI(Tl) scintillation crystal 7 having a diameter of 30 mm and a thickness of 2 mm receives fluorescence radiation from the irradiated sample. The scintillation crystal 7 is, in a conventional manner, coupled to a photo multiplier tube 8 whose output signals, by the intermediary of a preamplifier 9 and a linear amplifier 10, are impressed upon three single-channel analyzers 11, 12 and 13. The signal values registered in the signal channel analyzers are transmitted, by the intermediary of an analog-to-digital converter 14, to a computer 15. A mains supply 16 is provided to supply the photo multiplier tube and the electronic system with power.

Figure 3:
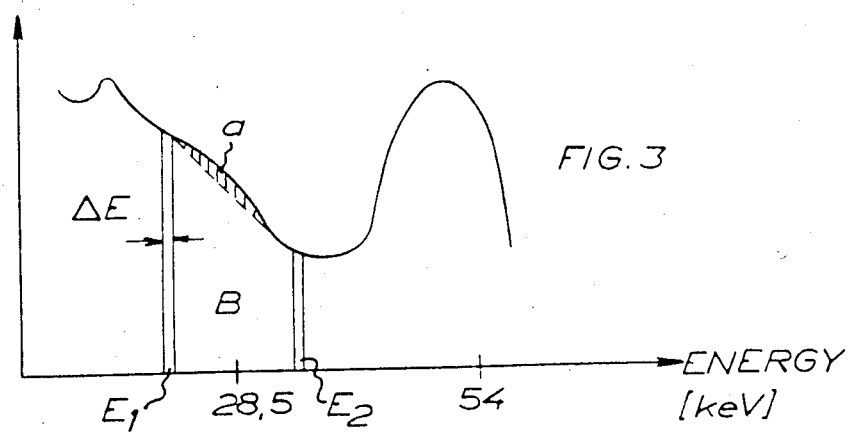

The mode of operation of the above-described apparatus is as follows. The single-channel analyzer 11 is set so as to register pulses in an energy interval $\Delta E$, which is centered about an energy value $E_1$. In the same manner, the single-channel analyzer 13 is operative to register pulses in an energy interval $\Delta E$ which is centered about an energy value $E_2$. The number of registered pulses in the interval about the value $E_1$ will be assumed to be $b_1$ and the number of registered pulses in the energy interval about the value $E_2$ will be assumed to be $b_2$. The single-channel analyzer 12 is operative to register pulses in the energy interval which lies between the above-mentioned two energy intervals. The number of pulses registered by the single-channel analyzer 12 will be assumed to be A. This number A represents, on the one hand, the background radiation which corresponds to the surface beneath the dotted line in the center interval and may be designated B, and, on the other hand, the characteristic X-ray radiation of the element whose content is to be determined. In FIG. 3, the number of pulses corresponding to the characteristic X-ray radiation is designated a. Thus, $a=A-B$, in which A is obtained from the single-channel analyzer 12 and B can be obtained by means of the numbers of pulses from the single-channel analyzers 11 and 13. For determining B, the dotted line portion of the pulse height distribution curve in FIG. 3 could be described by:

$$b(E) = k \cdot E^{-r} + c$$

in which r substantially determines the shape of the curve and can be determined once and for all and fixedly stored in the computer 15, and in which k and c are constants which can be automatically determined for each individual analysis using the values $b_1$ and $b_2$. These constants k and c substantially determine the position of the curve.

The constants k and c more precisely are given by the following expressions:

$$k = \frac{b_1 - b_2}{E_1^{-r} - E_2^{-r}}$$

$$c = b_1 - k \cdot E_1^{-r}$$

With the produced function, the number of pulses in the energy interval having the width $\Delta E$ can thus be determined. The total background B in FIG. 3 will thus be:

$$B = \left( k \cdot \left( E_1 + \frac{\Delta E}{2} \right)^{-r} + c \right) + \left( k \cdot \left( E_1 + \frac{3\Delta E}{2} \right)^{-r} + c \right) + \ldots + \left( k \cdot \left( E_1 + \frac{n \cdot \Delta E}{2} \right)^{-r} + c \right)$$

n can unambiguously be determined in that the following condition must be satisfied:

$$E_1 + \frac{n \cdot \Delta E}{2} = E_2 - \frac{\Delta E}{2}$$

n may be of the order of magnitude of 10.

The computer 15 is programmed such that, on the basis of the values $b_1$, $b_2$ and r, it determines the constants k and c and thereafter determines the number of background pulses B. Using the number of pulses B and the number of pulses A, the number of net pulses a is finally determined, which provides a measure of the concentration of the contrast agent in the irradiated sample volume.

The number of pulses in the energy interval across the three single-channel analyzers derives from Compton-scattered photons in the sample and is used in determinations in vivo for correction of varying sample volumes.

By designing the opening through which the source of radiation 1 irradiates the sample volume, as an elliptic aperture instead of a circular aperture, the radiation field will have an appearance which, on the one hand, prevents the first joint of the finger from being irradiated and, on the other hand, allows for lateral movement of the finger without the sensitivity of the apparatus being influenced.

By utilizing an NaI(Tl) detector, there will automatically be obtained an increase of the order of magnitude of 20% of the fluorescence rate of the characteristic radiation, this being dependent upon the resolution capacity of this detector with regard to the $K_\alpha$ and $K_\beta$ photons.

As illustrated in FIG. 5, the amplifier 9 which is connected to the output of the photo multiplier tube 8 may be an integrating rapid preamplifier and the linear amplifier 10 may have offset adjustment and adjustable amplification degree. The output of the amplifier 10 is connected to each of four comparators 17 each having its respective reference voltage which is produced by means of a precision voltage source 18 and four potentiometers 19. The output pulses from the comparators 17, which are generated in dependence upon the signal amplitude on the output of the photo multiplier 8, advance binary counters 21 step by step via bistable flip-flops 20. Using two monostable flip-flops 22 and 23, the length of the output pulses from the bistable flip-flops 20 and, as a consequence the counting frequency can be controlled. The counters 21 are in their turn connected to the microcomputer 15 which carries out the above-described calculations on the basis of the contents of the counters. It might be mentioned that one of the four comparators 17 corresponds to the above-mentioned energy interval across the three single-channel analyzers 11–13.

A great many modifications of the above-described embodiment of the apparatus according to the invention are possible without departing from the spirit and scope of the present invention.

To sum up, the present invention is extremely well suited for making quantitative analyses of the kinetics in vivo of iodine or barium-containing X-ray contrast agents. The apparatus may also be used for quantitative determination of the renal function both in vivo and in vitro by analysing the disappearance of iodic contrast agents from the blood (soft tissue). The determination may be made bloodlessly (by repeated measurements on one of the patient's ·finger tips), by analysing blood samples or by utilizing both methods. It will also be realized that the apparatus is useful for the determination of the contents of different elements, for which it is possible to eliminate the disturbance due to the iodine content in the NaI(Tl) scintillation detector. Thus, the apparatus is well suited for determining the mineral content of different matrices. It may also be employed for "onstream" analysis of the mineral content in an industrial production process for providing, for example, X-ray contrast agents. In the switch-over from analysis of one element to another, all energy intervals may be moved to the optimum positions in the pulse height distribution.

It might finally be mentioned that for adjustment of the angle between the primary radiation from the radiation source 1 and the radiation detected by the detector 7, 8, the radiation source 1 is mounted in a U-shaped holder 1a which can be swung about a horizontal axis passing through the tip of the finger.

What we claim and desire to secure by Letters Patent is:

1. An apparatus for determining the iodine content in a sample volume, characterized by a radiation source (1) that is $^{241}$Am and that excites the iodine in the sample volume with collimated radiation such that the iodine emits its characteristic X-ray radiation, an NaI(Tl) scintillation detector (7, 8) which is directed towards the sample volume for reception of X-ray radiation therefrom at an angle of approximately 135° in relation to the collimated excitation radiation directed towards the sample volume such that both the energy of Compton-scattered photons received from the sample volume and the difference between this energy and 28.5 keV differ substantially from the energy of the characteristic X-ray radiation of iodine, three single-channel analyzers (11, 12, 13) of which a first (12) register the number of pulses of the detector within a predetermined energy interval about the energy value for the characteristic X-ray radiation of iodine, and the other two (11, 13) register the number of pulses at the limits of said interval, and a calculating unit (15) for determining, from the two latter pulse numbers, the background radiation in said interval and for determining the iodine content from the difference between the pulse number of the first analyzer (12) and the pulse number representing the background radiation.

2. An apparatus according to claim 1, characterized in that the calculating unit (15) is operative to calculate the background radiation pulse number using the formula:

$$B = \left( k \cdot \left( E_1 + \frac{\Delta E}{2} \right)^{-r} + c \right) + \left( k \cdot \left( E_1 + \frac{3\Delta E}{2} \right)^{-r} + c \right) + \ldots + \left( k \cdot \left( E_1 + \frac{n \cdot \Delta E}{2} \right)^{-r} + c \right)$$

wherein $E_1$ is the energy level at one of said limits of said energy interval, $\Delta E$ is the number of pulses registered in an energy interval centered about the energy level $E_1$, r is a factor which subtantially determines the shape of the curve over said interval, and k, c and n are determined from the following expressions:

$$k = \frac{b_1 - b_2}{E_1^{-r} - E_2^{-r}}$$

$$c = b_1 - k \cdot E_1^{-r}$$

$$E_1 + \frac{n \cdot \Delta E}{2} = E_2 - \frac{\Delta E}{2}$$

where $E_2$ is the energy level at the other limit of said interval, and $b_1$ and $b_2$ are, respectively, the number of registered pulses in the energy interval $\Delta E$ centered about energy levels $E_1$ and $E_2$.

* * * * *